(12) United States Patent
Walker

(10) Patent No.: US 8,613,908 B2
(45) Date of Patent: Dec. 24, 2013

(54) SYSTEM AND METHOD FOR AUTHENTICATING PHARMACEUTICALS USING INTERNALLY LOCATED HYDROSCOPIC GELS WITH INDICIA

(76) Inventor: George F. Walker, New York, NY (US)

( * ) Notice: Subject to any disclaimer, the term of this patent is extended or adjusted under 35 U.S.C. 154(b) by 1223 days.

(21) Appl. No.: 12/111,503

(22) Filed: Apr. 29, 2008

(65) Prior Publication Data

US 2009/0269286 A1    Oct. 29, 2009

(51) Int. Cl.
*A61K 9/44* (2006.01)
(52) U.S. Cl.
USPC .......................................... 424/10.2
(58) Field of Classification Search
None
See application file for complete search history.

(56) References Cited

U.S. PATENT DOCUMENTS 5,992,742 A * 11/1999 Sullivan et al. .......... 235/462.01

* cited by examiner

*Primary Examiner* — Michael G Hartley
*Assistant Examiner* — Jennifer Lamberski
(74) *Attorney, Agent, or Firm* — Donald J. Ranft; Collen IP

(57) ABSTRACT

The invention is a pharmaceutical product which may be authenticated, comprising identifying markers disposed in the pharmaceutical product. The pharmaceutical product is selected from the group consisting of a pill, a tablet, a caplet, and a capsule. The identifying markers are gel pellets made from a hydroscopic medium having an indicia imprinted thereon and expand volumetrically when contacted with a liquid.

12 Claims, 6 Drawing Sheets

SYSTEM AND METHOD FOR AUTHENTICATING PHARMACEUTICALS USING INTERNALLY LOCATED HYDROSCOPIC GELS WITH INDICIA

FIELD OF THE INVENTION

The invention relates to a system and method for identifying the authenticity of pharmaceutical products.

BACKGROUND OF THE INVENTION

There is a vast market for medications aimed at a variety of physical afflictions affecting both animals and humans. Numerous medications are also on the market for a variety of plant diseases common to various kinds of trees, vegetables and the like. As a result, pharmaceutical industries have gown extensively over the past several decades, especially with the ever widening understanding of the human genome and the relationship of specific genes and their relation to a variety of illnesses. Many medications have become available for cures for both plant and animal diseases and illnesses, previously hard or impossible to treat effectively. In most cases the medications are carefully manufactured by leading pharmaceutical firms. However, there exists the danger of medications that are manufactured by rogue companies that are either incorrectly formulated or have falsified contents incorporated in the pills or capsules which are then purchased by consumers or dispensed at treating facilities such as hospitals, clinics and the like.

It is therefore of some interest as well as concern to find means for preventing counterfeiting of medications using methods that are not readily detectable by obvious methods such as visual examination of the exterior of the pill or capsule. See for example, U.S. Pat. No. 4,548,825 to Voss et al. which teaches a method of inkjet printing onto a pill or capsule. Identifying marks on the surface of such medications are too easily copied and counterfeited thereby allowing rogue manufacturers to utilize these symbols or marker present on the well known brand names on a counterfeited version of a particular medication.

The possibility of counterfeiting medications has increased in recent years as more domestic and foreign suppliers reach into the pharmaceutical supply chain thereby increasing the chances of making look-alikes. The ability to obtain drugs which are advertised as being authentic from the internet adds yet another source of possible counterfeit drugs in the form of pills and capsules that unsuspecting customers may have been induced to purchase. While some of the look-alikes may be equally as effective for the designated treatment as the originals, many will not be. Since there is the possibility that some counterfeit or look-alike pharmaceuticals may be ineffective, or worse yet, harmful or fatal to the plant or animal, it becomes prudent and even essential to have some internal hidden marker within the pharmaceutical from which authenticity of the individual pill or capsule can be ascertained. At the same time, this marker must be totally harmless to the plant or animal for which the use is intended.

SUMMARY OF THE INVENTION

The invention is an article of manufacture, comprising an identifying marker disposed in a pharmaceutical product. The pharmaceutical product may be selected from the group consisting of a pharmaceutical liquid, a pill, a tablet, a caplet, and a capsule. The identifying marker may be a hydroscopic medium having an indicia imprinted or embossed thereon, the identifying marker expandable volumetrically when contacted with a fluid.

The purpose of the present invention is to utilize a medium onto which a very small marker or indicia can be imparted or imprinted, the marked medium then inserted into each pill or capsule to be used for treatment purposes. Since the indicia or marker medium has to be extremely small in size to make it possible to insert into the pill or capsule, the indicia print or image must be sized in the sub-millimeter range. In addition, both the marker medium and the marker itself must be compatible with the animal or plant organisms' natural functions.

The present invention teaches that the marker medium expands on being immersed in a liquid medium, typically, though not necessarily, a water based medium in order to expand or enlarge the marker, logo, information content or indicia pattern.

It is an object of this invention to teach a method of authenticating a pharmaceutical product.

It is another object of the invention to teach a method of making and using an identifying marker.

It is also an object of the invention to teach an identifying marker that can be contained within a pharmaceutical product and expands with a pharmaceutical product and the identifying marker are placed in solution.

DESCRIPTION OF THE PREFERRED EMBODIMENTS

Figure 1A:
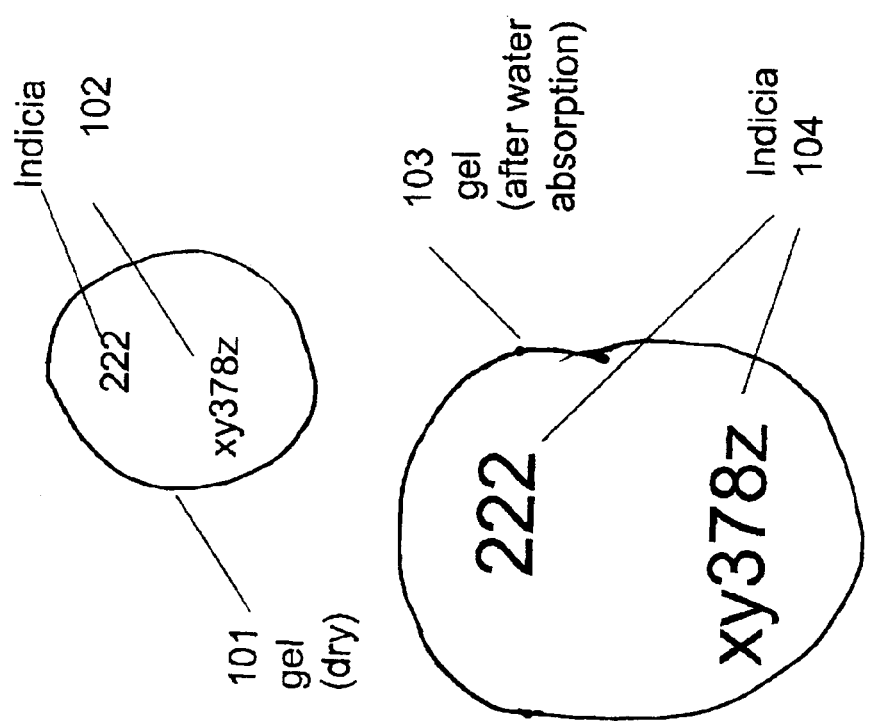
FIG. 1a shows a schematic of an identifying marker onto which indicia is imparted both before and after immersion is a fluid that leads to swelling.

The preferred embodiments of the present invention will now be described with reference to FIGS. 1 to 5 of the drawings. Identical elements in the various figures are identified with the same reference numerals.

The present invention addresses the need for an identification system and method of authentication of a pharmaceutical by utilizing a concealed identifying marker medium onto which is imparted identifying information, such as an indicia or logo that identifies the particular pharmaceutical and/or the manufacturer thereof. A most preferred identifying marker is a hydroscopic gel. In some cases the indicia may simply be that of the logo or other identification of the manufacturer. The indicia may be imparted onto the identifying marker by means such as transfer printing, laserjet printing, laser etching, extrusion or molding. Transfer printing or direct printing may use a dye in the form of a food coloring dye, known to be harmless to humans upon ingestion. The identifying marker may be in the form of a small spheroid, flat disk, or thread with major dimensions on the order one to two millimeters or less.

The individual symbols, logos or more detailed indicia imparted onto the identifying marker are typically on the order of 10's of microns in size. Once the indicia has been placed onto the identifying marker, it becomes mixed with the active and inactive ingredients of the medication, it becomes an integral part of the internally packaged portion of the pill or capsule.

When a question of authenticity arises, the pill or capsule is opened and its contents are removed and placed into a liquid, typically water. The identifying marker is preferably chosen to be hydroscopic so that water (or other liquids) becomes absorbed or adsorbed in it causing it to swell. This increase in size makes it possible to conveniently and simply determine the indicia on the identifying marker by eye, in some cases with the help of a magnifying glass or low powered microscope. Once so read, a determination can be made as to the authenticity of the medication.

Verifying the authenticity is particularly important for cases where the use of a bogus pharmaceutical pill or capsule may result in severe and unexpected side effects. In those cases, law suits are likely to arise in which the drug manufacturer faces possible heavy fines or even prison. In those extreme cases, knowing that the pharmaceutical manufacturer is liable is of utmost importance so that culpability or the lack thereof can be established using the identifying indicia of the present invention.

The use of medications in the form of pills or capsules is a multibillion industry and some counterfeiting of name brand drugs is not uncommon. In some cases theses counterfeit medications can cause considerable harm to the patient, be the patient, human, non-human or even in the form of plants. The present invention describes means for including identifying markers, preferably with a specific and unique identifying indicia imprinted onto the surface of the gel. The gel is then dispersed with the medication and filler material to form the pill or to fill the capsule. In some cases, these gels with identifying indicia can also be placed inconspicuously in certain liquid medication formulations so long as the liquid does not affect the physical properties of the identifying marker.

Authenticating a particular pharmaceutical can be achieved by dispersing the contents of the capsule, pill, caplet or tablet containing the pharmaceuticals and the marker with imprinted indicia. The caplet or tablet is placed in a liquid medium which is absorbed or adsorbed by the hydroscopic marker gel. The marker gel may then be retrieved from the liquid medium for examination by a microscope, hand lens or other well known optical techniques such as spectroscopic examination, laser scanning with appropriate optical receivers. A comparison of the indicia is then made with a standard marker provided by the manufacturer. Typical volumes of the indicia prior to immersion in the hydroscopic medium are in the range $10^{-6}$ to $10^{-2}$ cm$^3$. After absorption or adsorption of the hydroscopic medium the volume will be increased by factors of 5 to 100.

The identifying marker of the present invention may be made from any material suitable for the purposes described here in. The material should be nontoxic to the human or mammal is so that it can be consumed readily without any adverse effects. In addition, it is preferable that the material swells when it is placed in contact with water or other solution. However, it is contemplated that materials that do not swell could also be suitable for you in the invention for certain applications. In this case, identification of the identifying marker would probably be made with a microscope or magnifying glass.

Gelatin is the preferred material to make the identifying markers. There are hydrogels gels such as poly-etheramidoamines that have swelling degree in H$_2$O higher than 500%. In addition, there are other polyacrylamide and polybutadiene gels, that could be suitable, so long as they do not have toxic effects.

Other materials suitable for the identifying marker material are those that can swell when they adsorb or absorb solvents, such as water. An example of that is the fibrous material used in baby or adult disposable diapers. Another example is the permeable material used in contact lenses.

Gelatin is a protein laden (amino acids) material produced by partial hydrolysis of the skin and bone and connective tissue of animals usually after slaughter. It is a translucent brittle solid substance which melts when heated and solidifies when cooled. Together with water it forms a semi-solid colloidal gel. Agar and Pectin are edible Gelatins.

A hydrogel is a colloidal gel in which water is the dispersion medium. A colloidal gel is colloid in a more solid form than a sol. In a hydrogel there are networks of polymer chains that are water insoluble. Common ingredients are e.g. polyvinyl alcohol, sodium polyacrylate, acrylate polymers and copolymers with an abundance of hydrophilic groups. After polymerization the hydrophilic gel (Gelatin) is brought in contact with water and the network swells and expands.

The invention utilizes small pellets, tabs or threads of gel material onto which a distinguishing marker or indicia is imparted by any one of many well known methods. As examples, the indicia may be imprinted by means of transfer printing from a roller, etched or printed by means of photolithography and an appropriate etching material or printing ink, chemical etching, reactive ion etching, laser printing, embossing as well as other techniques well known by those skilled in the art.

FIG. 1a shows examples of the tab or pellet in two of its states relevant to the present invention. Pellet (tab) 101 is a hydroscopic gel material as shown in its normal physical state. It is shown after an indicia 102 has been imparted onto at least one of its surfaces. Pellet 101 is also shown after absorption of water or other fluid as indicated by 103. The absorption of water or other fluids causes an increase in the size of pellet 101 thereby increasing its dimensions by way of swelling. Pellet 101 becomes transformed from the original get pellet into a much larger pellet 103 and the indicia on 103 are shown as 104 having been proportionately increased in size compared to indicia 102 due to the swelling of 101 into 103. The degree of swelling can be as much as a linear dimensional factor of from 5 to 100 times, preferably 5 to 20 times.

Figure 1B:
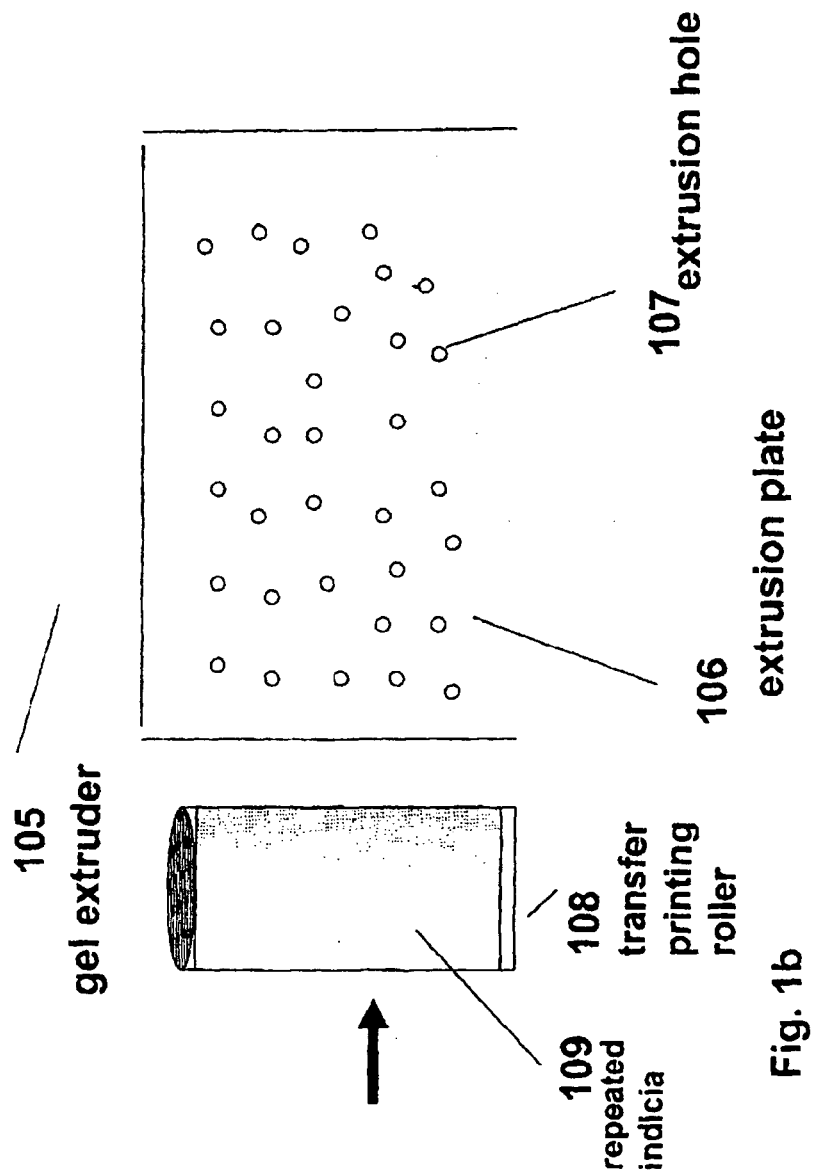
FIG. 1b is a typical gel extruder with an extrusion plate to form small gel pellets which become marked by means of transfer printing from a roller.

FIG. 1b gives one representation of how such small gel pellets/tabs can be formed. A gel extruder 105 is periodically pressurized to extrude gel into extrusion holes or orifices 107 on the extrusion front plate 106. Indicia in this example are imparted by transfer printing using transfer printing roller 108. Roller 108 containing a repeated series of the desired indicia 109 is rolled over plate 106 and the extruded gel residing in the holes 107. In this manner the indicia are transferred using an appropriate ink or transfer medium.

Figure 2:
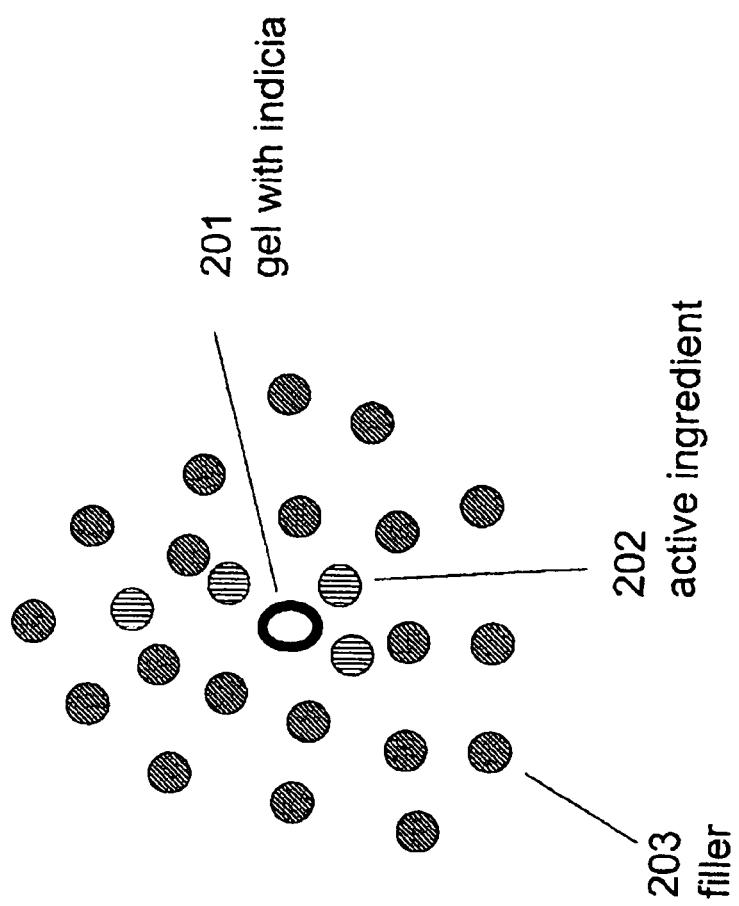
FIG. 2 is a schematic indicating the components that are part of the proposed capsule or pill consisting of the filler material, the medication material and the identifying marker material containing the indicia.

Gel pellets with indicia 201 are shown in FIG. 2. Also shown are the additional components that typically constitute a pill, tablet or capsule. A major portion of the pill, tablet or capsule contains a filler 203 in addition to the active medical ingredient 202. In order to produce a tablet or capsule, ingredients 202 and 203 are compacted by pharmaceutical companies using well known compressing machines for pills, caplets and tablets and a combination of pressing and filling machines for capsules. The present invention includes a third component 201 which is combined along with conventional components 202 and 203 and then processed to form capsules and pills in the same way as though 201 were not present. A single pellet 201 may have a volume in the range 10 to 102 cm³. This size range will not affect the customary components of the tablet or capsule in any significant way. In general, a single capsule will contain many elements 202 and 203. More than one element 201 is commonly present in a single capsule as well.

Figure 3:
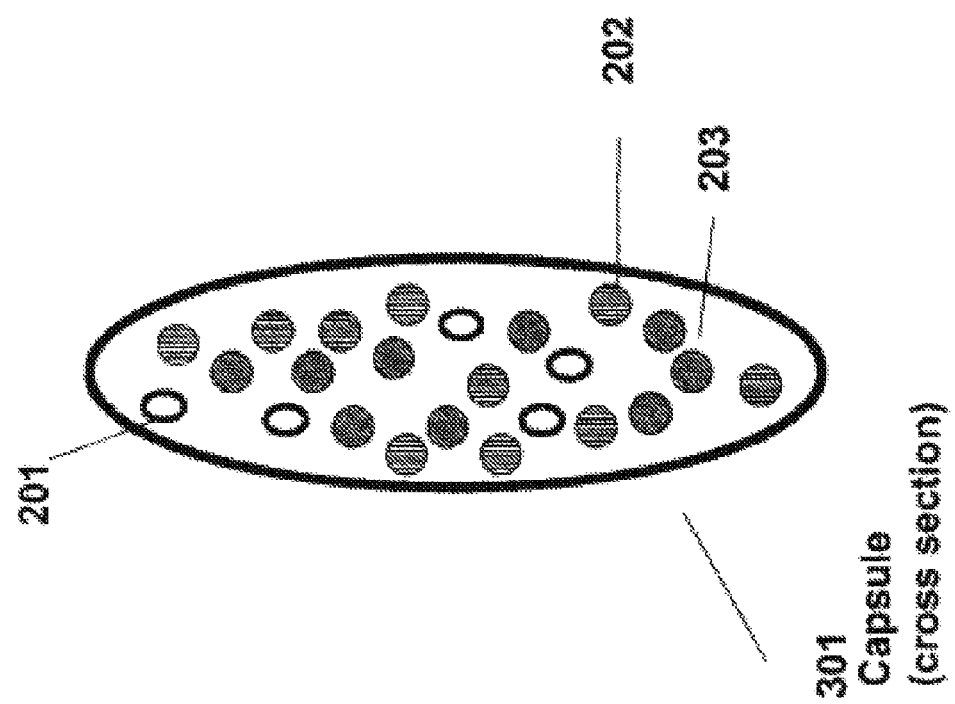
FIG. 3 shows a cross-section of a capsule with the three ingredients.

A representative cross-section of a capsule 301 containing gel with indicia 201, active ingredient 202, and filler 203 is shown in FIG. 3. While only a relatively few gel with indicia 201, active ingredient 202, and filler 203 are shown for clarity, it is understood by those skilled in the art that the capsule, pill or tablet contains identifying markers and that are preferably compressed. The advantage of having numerous gels with indicia 201 in capsule 301 is to enhance ease in authenticating the pharmaceutical medication should it become necessary. A plurality of gels with indicia 201 in a single capsule or tablet greatly simplifies finding any single gel with indicia 201 with the sought after indicia for the purpose of authenticating the pharmaceutical.

With the variables of size, color, shape and marking techniques (alpha numerics, bar codes, dot codes, etc) the laundry list of possibilities is almost endless. Extrusions can be made with multiple colors and everything from batch numbers to secret codes can be applied by embossing or micro printing etc. There can be more than one type of identifying markers in each medication and these markers may be combined with other ingredients in many medications that hasten the break up (dissolution) of the medication thus making identification faster and easier for both the pharmacist or the patient at home.

In general, there can also be more than one specific indicia on a marker tab or pellet in a single pharmaceutical capsule. Multiple distinguishing indicia on separate tabs or pellets can be used to identify various aspects of the pharmaceutical. For example there can be data relating to dosage, date of manufacture, location of manufacturing facility and the like. Some of these markers can be individually color coded to reveal specific desired information in addition, some may not be digestible but innocuous to the animal so that the marker can be recovered intact in the feces for identification purposes.

Figure 4:
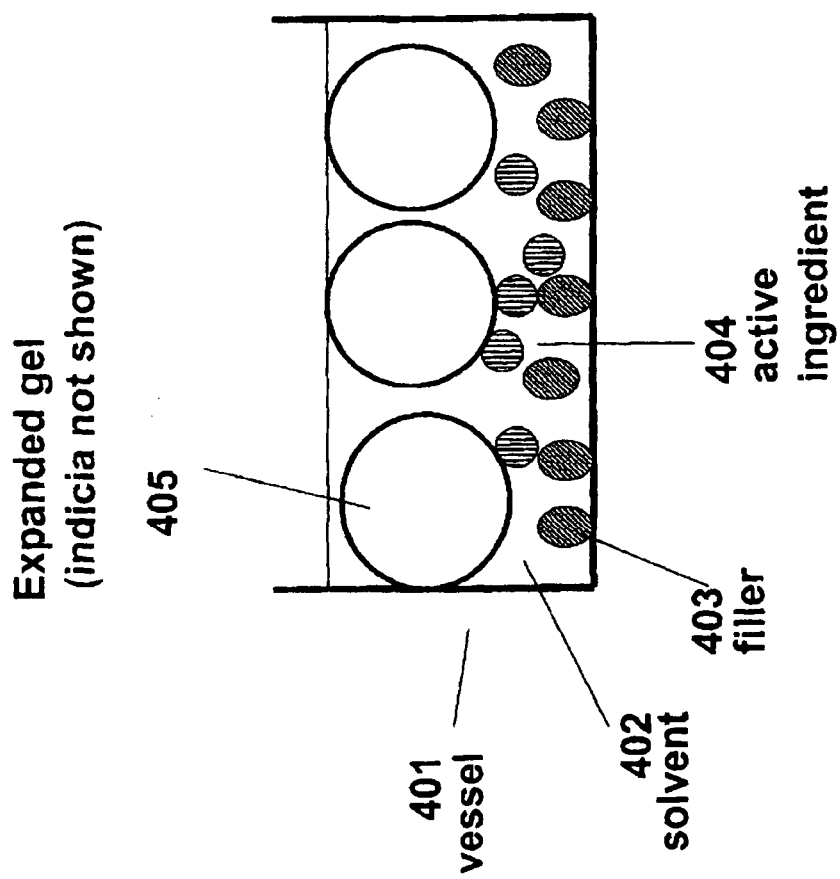
FIG. 4 shows three ingredients of a capsule solvent to cause swelling of the identifying marker.
Figure 5:
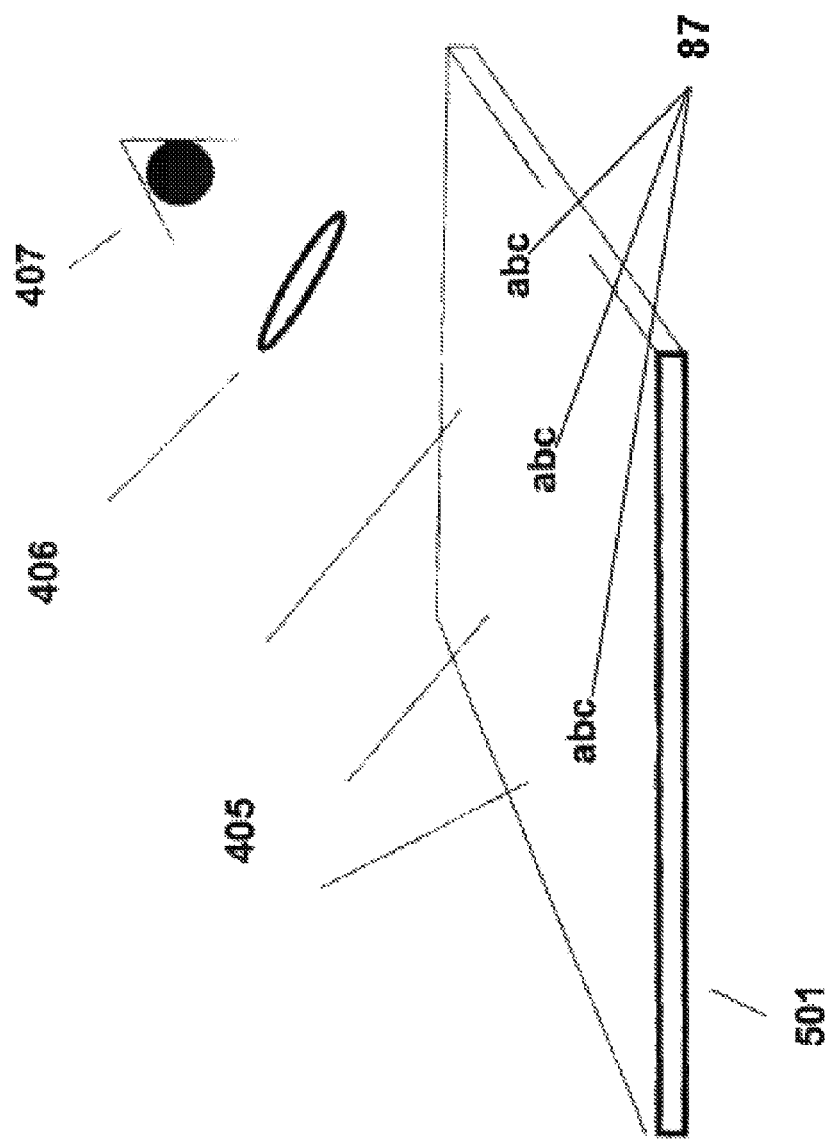
FIG. 5 shows an expanded view of an identifying marker being viewed through a magnifying apparatus.

Authenticating is undertaken by emptying the contents of capsule 301 into solvent 402 in vessel 401, with water the most natural solvent; however other solvents may absorb used depending on the particular gel. For example, other solvents can be alcohols, protein solutions or other compatible liquids with the specific requirements for the swelling of the gels. In general filler 403 and active ingredient 404 will either dissolve or sink to the bottom of a container with a hydroscopic solvent. On the other hand, gel 405 will expand due its hydroscopic property causing gel 405 to expand in volume as previously illustrated in FIG. 1. Due to the density of gels, the swollen gel will rise to the top of solvent 402 from which one or more of the gel labels can be simply retrieved for further examination of its indicia. The expansion will also affect the indicia illustrated in FIG. 5. After dispersing the contents in water or other suitable solvent, the expanded gel 405 of FIG. 4 is removed from vessel 401 and is examined by eye 407 on surface 501 shown in FIG. 5 using a simple magnifying glass 406 or other positive lens. In some cases a microscope may be used in order to interpret the indicia of 405 thereby completing the authentication process. Spectroscopic examination may also be used to identify mater 405 with indicia 87.

EXAMPLE

A common form of Gelatin was used to make a hydroscopic gel marker. Gelatin dessert (Jello®) was used to make a very high concentration of the material in boiling water. The solution (sol) was allowed to cool at room temperature and after solidification the gel was further densified by air drying. The material then had the density of hard rubber, and from this material small pieces were sliced. Small coin-shaped gel markers were made with logo indicia markers by extruding the partially cooled gel through a syringe with a tuberculin needle that was deformed at the tip to make a non-annular shape. This shape was the equivalent of a logo. This long, small diameter (less than 50 microns) thread was then further cooled and densified. Then thin slices were microtomed from it to produce the small logoed coin shaped pieces. These were then dumped in a dish of cold water and their subsequent swelling was observed.

Although this invention has been described with a certain degree of particularity, it is to be understood that the present disclosure has been made only by way of illustration and that numerous changes in the details of construction and arrangement of parts may be resorted to without departing from the spirit and the scope of the invention.

We claim:

1. A pharmaceutical product which may be authenticated, comprising:
    identifying markers disposed in the pharmaceutical product, the pharmaceutical product having an interior and containing active and inactive ingredients,
    wherein the pharmaceutical product is selected from the group consisting of a pill, a tablet, a caplet, and a capsule,
    the identifying markers comprise a plurality of gel pellets integrally mixed with the active and inactive ingredients and the gel pellets reside in the interior of the pharmaceutical product,
    the gel pellets are made from a hydroscopic medium and have a shape, a color, and an indicia imprinted thereon, the indicia being alpha numeric characters, dot codes, or logos,
    and wherein when the contents of the pharmaceutical product are dispersed in a liquid medium for authentication, the gel pellets expand volumetrically when contacted with the liquid medium so that the shape, the color, and the indicia are visible to a human eye and can be used to visually verify the pharmaceutical product.

2. The pharmaceutical product of claim 1, wherein the indicia on said gel pellets is used to authenticate the pharmaceutical by comparison with a standard indicia.

3. The pharmaceutical product of claim 1, wherein the indicia on said gel pellets is imparted with a scanning laser or micro-embossing.

4. The pharmaceutical product of claim 1, wherein the indicia on said gel pellets is created with a laser printer or an ink jet printer.

5. The pharmaceutical product of claim 1, wherein the indicia on said gel pellets is chemically etched through a mask.

6. The pharmaceutical product of claim 1, wherein the indicia on said gel pellets is etched using reactive ion etching.

7. The pharmaceutical product of claim 1, wherein said gel pellets are non-toxic for human consumption.

8. The pharmaceutical product of claim 1, wherein the gel pellets are non-digestible for identification of the identifying markers in feces.

9. The pharmaceutical product of claim 1, wherein each gel pellet has a volume and the volume is in the range of $10^{-6}$ to $10^{-2}$ cm³.

10. The pharmaceutical product of claim 1, wherein the gel pellets are retrievable without damage.

11. The pharmaceutical product of claim 10, wherein the gel pellets expands volumetrically by a factor of 5 to 100.

12. The pharmaceutical product of claim 1, wherein the pharmaceutical product further comprises at least one other identifying marker.

* * * * *